United States Patent [19]

Wasley

[11] Patent Number: 4,737,496
[45] Date of Patent: Apr. 12, 1988

[54] 1,3,4,16B-TETRAHYDRO-2H,10H-INDOLO[2,1-C]PYRAZINO-[1,2-A][1,4]BENZODIAZEPINES USEFUL AS SEROTONIN-2 RECEPTOR ANTAGONISTS

[75] Inventor: Jan W. F. Wasley, Chatham, N.J.

[73] Assignee: Ciba-Geigy Corporation, Ardsley, N.Y.

[21] Appl. No.: 914,028

[22] Filed: Oct. 1, 1986

[51] Int. Cl.$^4$ .................... A61K 31/33; C07D 487/12
[52] U.S. Cl. .................................. 514/219; 540/492; 540/555
[58] Field of Search ................. 540/492, 555; 514/219

[56] References Cited

U.S. PATENT DOCUMENTS

| | | | |
|---|---|---|---|
| 4,192,803 | 3/1980 | Wright et al. | 514/220 |
| 4,316,900 | 2/1982 | Wasley | 514/219 |
| 4,362,666 | 12/1982 | Wasley | 540/555 |
| 4,424,221 | 1/1984 | Wasley | 514/219 |
| 4,529,724 | 7/1985 | Ho | 514/219 |
| 4,547,497 | 10/1985 | Ho | 514/219 |
| 4,587,244 | 5/1986 | Ho | 514/219 |
| 4,596,799 | 6/1986 | Wasley | 514/219 |

OTHER PUBLICATIONS

J. Med. Chem. 29, 1118–1121 (1986).
J. Het. Chem. 20, 1565–1569 (1983).
Usan and USP Dictionary of Drug Names (1987) p. 32.
Society for Neuroscience Meeting Abstracts vol. 9, p. 436 (1983) Abstract No. 128.9.
Life Sciences 32, 355–363 (1983).
British J. Pharmacol. 86 (Suppl.) 1985, p. 743P.

Primary Examiner—Donald G. Daus
Assistant Examiner—Cecilia Shen
Attorney, Agent, or Firm—Norbert Gruenfeld

[57] ABSTRACT

The invention relates to 1,3,4,16b-tetrahydro-2H,10H-indolo[2,1-c]pyrazino[1,2-a][1,4]benzodiazepine derivatives of the formula I,

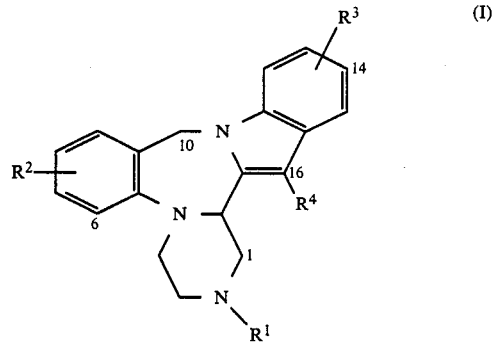

wherein $R^1$ is hydrogen, lower alkyl, $C_{3-7}$-alkenyl, $C_{3-7}$-alkynyl, 3 to 7 ring-membered cycloalkyl, $C_{2-7}$-alkyl substituted by a substituent selected from hydroxy, amino, N-mono-lower alkyl-amino and N,N-di-lower alkyl-amino; or $R^1$ is lower alkyl substituted by a substituent selected from 3 to 7 ring-membered cycloalkyl, carboxy, lower alkoxycarbonyl, carbamoyl, N-mono-lower alkyl-carbamoyl, N,N-di-lower alkyl-carbamoyl and lower alkanoyl; or $R^1$ is lower alkyl substituted by either phenyl or benzoyl each of said phenyl or benzoyl radicals being unsubstituted or substituted by up to three members selected from lower alkyl, lower alkoxy, lower alkylthio, halogen and trifluoromethyl; $R^2$ and $R^3$ represent hydrogen, lower alkyl, hydroxy, lowr alkoxy, halogen or trifluoromethyl; and $R^4$ represents hydrogen, lower alkyl, hydroxy-lower alkyl, carboxy, lower alkoxycarbonyl, carbamoyl, N-mono- or N,N-di-lower alkyl-carbamoyl, or formyl; salts and 2N-oxides; which are useful as serotonin-2 receptor antagonists.

15 Claims, No Drawings

1,3,4,16B-TETRAHYDRO-2H,10H-INDOLO[2,1-C]PYRAZINO-[1,2-A][1,4]BENZODIAZEPINES USEFUL AS SEROTONIN-2 RECEPTOR ANTAGONISTS

SUMMARY OF THE INVENTION

The present invention relates to 1,3,4,16b-tetrahydro-2H,10H-indolo[2,1-c]pyrazino[1,2-a][1,4]benzodiazepine derivatives, useful as serotonin-2-receptor antagonists and as therapeutic agents for the treatment of disorders responsive thereto, processes for preparing same, pharmaceutical compositions comprising said compounds, and methods of treating syndromes, conditions and diseases in mammals responsive to the effect of such a serotonin receptor antagonist by administration of said compounds or a pharmaceutical composition comprising said compounds.

DETAILED DESCRIPTION OF THE INVENTION

The invention relates to 1,3,4,16b-tetrahydro-2H,10H-indolo[2,1-c]pyrazino[1,2-a][1,4]benzodiazepine derivatives of the formula I,

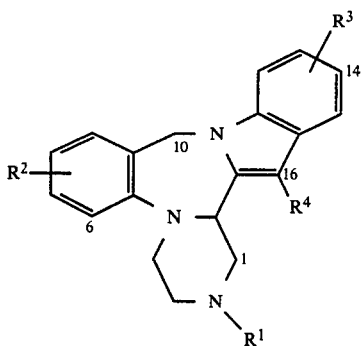

(I)

wherein $R^1$ is hydrogen, lower alkyl, $C_{3-7}$-alkenyl bonded on a saturated carbon, $C_{3-7}$-alkynyl bonded on a saturated carbon, 3 to 7 ring-membered cycloalkyl, $C_{2-7}$-alkyl substituted by a substituent selected from hydroxy, amino, N-mono-lower alkyl-amino and N,N-di-lower alkyl-amino wherein said substituents are separated from the ring nitrogen atom by at least 2 carbon atoms; or $R^1$ is lower alkyl substituted by a substituent selected from 3 to 7 ring-membered cycloalkyl, carboxy, lower alkoxycarbonyl, carbamoyl, N-mono-lower alkyl-carbamoyl, N,N-di-lower alkyl-carbamoyl and lower alkanoyl; or $R^1$ is lower alkyl substituted by either phenyl or benzoyl each of said phenyl or benzoyl radicals being unsubstituted or substituted by up to three members selected from lower alkyl, lower alkoxy, lower alkylthio, halogen and trifluoromethyl; $R^2$ and $R^3$, independently of one another, represent hydrogen, lower alkyl, hydroxy, lower alkoxy, halogen or trifluoromethyl; and $R^4$ represents hydrogen, lower alkyl, hydroxy-lower alkyl, carboxy, lower alkoxycarbonyl, carbamoyl, N-mono- or N,N-di-lower alkyl-carbamoyl, or formyl; salts, particularly pharmaceutically acceptable salts thereof; and the 2-N-oxides of said compounds wherein $R^1$ has meaning as defined above but does not represent hydrogen.

Preferred are the compounds of formula I wherein $R^1$ represents hydrogen, lower alkyl, $C_3-C_7$ lower alkenyl bonded on a saturated carbon atom or $C_2-C_7$-alkyl substituted by hydroxy; $R^2$ and $R^3$ independently represent hydrogen, lower alkyl, lower alkoxy, halogen or trifluoromethyl; $R^4$ represents hydrogen, lower alkyl, hydroxymethyl, carbamoyl, N-mono- or N,N-di-lower alkylcarbamoyl, carboxy or lower alkoxycarbonyl; pharmaceutically acceptable salts thereof; and 2-N-oxides of said compounds wherein $R^1$ is as defined above but does not represent hydrogen.

Further preferred are the compounds of the formula I wherein $R^1$ represents hydrogen or lower alkyl; $R^2$ represents hydrogen, lower alkyl, halogen or trifluoromethyl; $R^3$ represents hydrogen, lower alkyl, halogen, trifluoromethyl or lower alkoxy; $R^4$ represents hydrogen, lower alkyl, hydroxymethyl, carboxy, carbamoyl, N-mono- or N,N-di-lower alkylcarbamoyl or lower alkoxycarbonyl; and pharmaceutically acceptable salts thereof.

Particularly preferred are the compounds of formula I wherein $R^1$ represents hydrogen or lower alkyl; $R^2$ represents hydrogen or halogen; $R^3$ represents hydrogen, lower alkoxy or halogen; $R_4$ represents carboxy, lower alkoxycarbonyl, carbamoyl or N-mono- or N,N-di-lower alkyl-carbamoyl; and pharmaceutically acceptable salts thereof.

A further particularly preferred embodiment relates to the compounds of formula I wherein $R^1$ represents hydrogen or lower alkyl; $R^2$ represents hydrogen or halogen; $R^3$ represents hydrogen, lower alkoxy or halogen; $R^4$ represents lower alkoxycarbonyl or carbamoyl; and pharmaceutically acceptable salts thereof.

Most preferred are said compounds of formula I wherein $R^1$ represents lower alkyl; $R^2$ and $R^3$ represent hydrogen; $R^4$ represents lower alkoxycarbonyl; and pharmaceutically acceptable salts thereof.

In the context of the present application the term "lower" designates radicals having up to and including 7, preferably up to and including 4 carbon atoms. In terms like "lower alkoxycarbonyl" the term "lower" applies only to the alkoxy moiety.

Lower alkyl is preferably $C_1-C_4$-alkyl, advantageously methyl or propyl. $C_{3-7}$-alkenyl and $C_{3-7}$-alkynyl bonded on a saturated carbon are for example allyl and propargyl, respectively.

3 to 7 Ring-membered cycloalkyl (as in $R^1$) is for example cyclohexyl.

$C_{2-7}$-alkyl substituted by a substituent selected from hydroxy, amino, N-mono-lower alkyl-amino and N-di-lower alkyl-amino wherein said substituents are separated from the ring nitrogen atom by at least 2 carbon atoms (as in $R^1$) is for example 2-(hydroxy, amino, methylamino or dimethylamino)-ethyl.

Lower alkyl substituted by a substituent selected from 3 to 7-ring membered cycloalkyl, carboxy, lower alkoxycarboyl, carbamoyl, N-mono- lower alkyl-carbamoyl, N,N-di-lower alkyl-carbamoyl and lower alkanoyl (as in $R^1$) is for example (cyclohexyl, carboxy, methoxycarbonyl, carbamoyl, N-methyl-carbamoyl, N,N-dimethyl-carbamoyl or acetyl)methyl.

Lower alkyl substituted by either phenyl or benzoyl each of said phenyl or benzoyl radicals being unsubstituted or substituted by up to three members selected from lower alkyl, lower alkoxy, lower alkylthio, halogen and trifluoromethyl (as in $R^1$) is for example benzyl, benzoyl-methyl, p-methyl-benzyl, p-methoxy-benzyl, p-methylthio-benzyl, p-chloro-benzyl, p-trifluoromethyl-benzyl, (p-methyl-benzoyl)-methyl, (p-methoxy-benzoyl)-methyl, (p-methylthio-benzoyl)-methyl, (p- chloro-benzoyl)-methyl or (p-trifluoromethyl-benzoyl)-methyl.

Lower alkyl (as in $R^2$, $R^3$ or $R^4$) is for example methyl. Lower alkoxy (as in $R^2$ or $R^3$) is for example methoxy.

Halogen (as in $R^2$ or $R^3$) is for example chloro.

Hydroxy-lower alkyl (as in $R^4$) is preferably hydroxymethyl. Lower alkoxy-carbonyl ($R^4$) is preferably methoxycarbonyl. N-mono-lower alkyl-carbamoyl (as in $R^4$) is preferably N-methyl-carbamoyl. N,N-di-lower alkyl-carbamoyl (as in $R^4$) is preferably N,N-dimethyl-carbamoyl.

The compounds of the formula I are capable of forming acid addition salts, preferably pharmaceutically acceptable acid addition salts, for example salts of inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid; or amino acids, such as arginine and lysine.

Acidic compounds of the formula I, e.g. wherein $R^4$ represents carboxy or wherein $R^1$ is carboxy-lower alkyl, are capable of forming metal or ammonium salts, preferably pharmaceutically acceptable and non-toxic metal or ammonium salts, for example alkali metal or alkaline earth metal salts, for example sodium, potassium, magnesium or calcium salts, or salts with ammonia or suitable organic amines-aliphatic, cycloaliphatic, cycloaliphatic-aliphatic or araliphatic primary, secondary or tertiary mono-, di- or poly-amines and also heterocyclic bases being especially suitable for the salt formation—such as lower alkylamines, for example triethylamine, hydroxy-lower alkylamines, for example 2-hydroxyethylamine, bis-(2-hydroxyethyl)-amine, 2-hydroxyethyldiethylamine or tri-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dizenbylethylenediamine, and also bases of the pyridine type, for example pyridine, collidine or quinoline. Compounds of the formula I having a free carboxy group may also be in the form of internal salts, that is to say in zwitterionic form.

Compounds of the formula I having more than one basic and/or acidic group may form poly-salts or one part of the molecule may be in the form of an internal salt and another part may be in the form of a normal salt.

Examples for compounds having more than one basic group are compounds of the formula I wherein $R^1$ represents $C_{2-7}$-alkyl substituted by amino, N-mono-lower alkyl-amino or N,N-di-lower alkyl-amino.

For isolation or purification it is also possible to use pharmaceutically unacceptable salts. However, only the pharmaceutically acceptable non-toxic salts are used therapeutically and these are therefore preferred.

The compounds of the invention are useful in mammals, primarily as serotonin-2 receptor antagonists and as therapeutic agents for the treatment of disorders and conditions which are responsive to the action of a serotonin-2 receptor antagonist, including disorders of the central nervous system, the cardiovascular system and the gastrointestinal system.

The above-cited properties are demonstrable in vitro and in vivo tests, using advantageously mammals, e.g. rats, dogs, monkeys or isolated organs, tissues and preparations thereof. Said compounds can be applied in vitro in the form of solutions, e.g. preferably aqueous solutions, and in vivo either enterally or parenterally advantageously orally or intravenously, e.g. within gelatin capsules, as starch suspensions or in aqueous solutions. The dosage in vitro may range between about $10^{-6}$ molar and $10^{-9}$ molar concentrations. The dosage in vivo may range between about 0.10 and 30 mg/kg/day, preferably between about 0.50 and 20 mg/kg/day, advantageously between about 1.0 and 10 mg/kg/day.

The compounds described above are active e.g. in the following test systems indicative of serotonin-2 receptor antagonism:

The serotonin-2 receptor (also named 5-hydroxytryptamine-2 or 5HT-2 receptor) binding properties are determined in vitro by measuring the ability of said compounds to inhibit the specific binding of $^3$H-ketanserin, in membrane preparations of frontal/parietal cortex from male Sprague-Dawley rats essentially as described by Battaglia et al. in Life Sciences 33, 2011 (1983). $IC_{50}$ values, representing the concentration of compound required to displace 50% of of $^3$H-ketanserin, are determined by log-logit analysis of the specific binding data.

Illustrative of the invention, the compound of example 1 is effective in the serotonin-2 receptor binding assay having an $IC_{50}$ value of about 4 nM.

Selectivity for the 5HT-2 receptors can be determined by also measuring specific binding to serotonin-1 (5HT-1) receptors, e.g. according to Middlemiss, D. N. and Fozard, J. R. in Eur. J. Pharmacol. 90, 151 (1980).

In vivo, the compounds according to the present application displace the binding of $^3$H-spiperone to serotonin-2 receptors in rat brain. Illustrative of the invention, the compound of example 1 displaces the binding of $^3$H-spiperone with an $ED_{50}$ value of about 2 mg/Kg i.p.

The serotonin-2 antagonism or blockade is demonstrated in vivo by measuring the inhibition of the head twitch induced by 5-hydroxytryptophane (the metabolic precursor of serotonin) in the rat. The head twitch test for assessing central nervous system serotonin-2 receptor antagonism in the rat is described in Neuropharmacology 16, 663 (1977) and in J. Pharmacol. Exp. Ther. 228, 133 (1984). The test is carried out as follows:

Male Wistar rats (120–180 g) are fasted for 18 hours prior to testing but allowed water ad libitum. All animals are pretreated with the peripheral decarboxylase inhibitor alpha-methyl-DOPA hydrazine (carbidopa, 25 mg/kg i.p., 4.0 ml/kg) followed 30 minutes later by 5-hydroxy-tryptophane (5-HTP 100 mg/kg s.c., 4.0 ml/kg). Ninety minutes after receiving 5-HTP, the rats are placed individually in plexiglass observation cages and the frequency of head twitches for each animal is counted over a 10 minute observation period. The test compound or vehicle is administered at either 0.5 hour at 1.0 ml/kg i.p. or at 1, 2 or 4 hours at 10 ml/kg p.o. prior to the observation period. $ED_{50}$ values are determined by probit analysis.

Illustrative of the invention, the compound of example 1 is effective in the head twitch test at a dose about 3 mg/kg p.o. in the rat.

Further biological effects of the compounds of the invention attributable to the serotonin-2 receptor blocking properties of the compounds, e.g. effects on the central nervous and cardiovascular systems, can be determined using animal tests well-known in the art. For example, effects indicative of anxiolytic properties may be seen in the standard Cook-Davidson conflict model in the rat; an increase in punished operant performance is indicative of an anti-anxiety effect. Antihypertensive properties can be demonstrated in the spontaneous hypertensive rat. Antithrombotic effects can be demonstrated by the inhibition of serotonin-induced platelet aggregation.

The aforesaid advantageous properties render the compounds of the invention useful in mammals, especially as serotonin-2 receptor antagonists, for the treatment of central nervous system disorders such as anxiety, depression and mania, for the treatment of gastrointestinal disorders such as ulcers, and for the treatment of cardiovascular disorders such as hypertension and thrombosis.

The compounds of the present application which inhibit serotonergic function at central serotonin-2 receptors are contemplated to be particularly useful as anxiolytic agents for the treatment of anxiety particularly as such cause little or no sedation or impairment of performance at effective anxiolytic doses.

The compounds of the formula I, the 2-N-oxides, and salts thereof are manufactured using the following processes:

(a) a compound of the formula II,

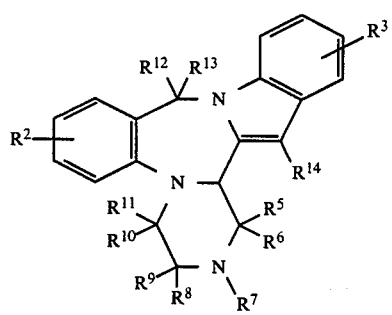

wherein $R^2$ and $R^3$ have the meanings given above; each of $R^5$ and $R^6$ represents hydrogen, or $R^5$ and $R^6$ together represent oxo; $R^7$ has meaning of $R^1$ and represents preferably hydrogen, lower alkyl, $C_{2-7}$-alkyl substituted by hydroxy, amino or mono- or di-lower alkyl-amino, $C_{3-7}$-alkenyl, $C_{3-7}$-alkynyl, or lower alkyl substituted by 3 to 7-ring membered cycloalkyl or optionally substituted phenyl; each of $R^8$ and $R^9$ represents hydrogen, or $R^8$ and $R^9$ together represent oxo; each of $R^{10}$ and $R^{11}$ represents hydrogen or $R^{10}$ and $R^{11}$ together represent oxo; each of $R^{12}$ and $R^{13}$ represents hydrogen or $R^{12}$ and $R^{13}$ together represent oxo; and $R^{14}$ has meaning of $R_4$ given above and represents preferably hydrogen, lower alkyl which may be substituted by hydroxy, or lower alkoxycarbonyl; with the proviso that at least one oxo group represented by $R^5$ and $R^6$, $R^8$ and $R^9$, $R^{10}$ and $R^{11}$ or $R^{12}$ and $R^{13}$ is present; is treated with a suitable reducing agent capable of converting said oxo group into a methylene group; or (b) a compound of the formula III

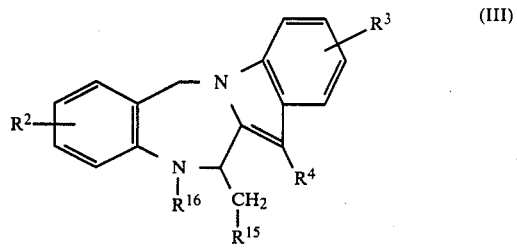

wherein $R^{15}$ represents a leaving group X, and $R^{16}$ represents the group —$CH_2$—$CH_2N(R^7)$—H wherein $R^7$ represents hydrogen, lower alkyl, $C_{2-7}$-alkyl substituted by hydroxy which may be protected by a hydroxy-protecting group, $C_{2-7}$-alkyl substituted by aminio or mono-lower alkyl-amino each of which is protected by an amino-protecting group, $C_{2-7}$-alkyl substituted by di-lower alkyl-amino, or $R^7$ represents $C_{3-7}$-alkenyl, $C_{3-7}$-alkynyl or 3 to 7 ring-membered cycloalkyl; or a compound of formula III wherein $R^{15}$ represents the group —NH—$R^7$ as defined above and $R^{16}$ represents the group —$CH_2$—$CH_2$—X where X represents a nucleophilic leaving group; or a compound of formula III wherein $R^{15}$ represents the group —N($R^7$)—$CH_2$—$CH_2$—X where the substitutents have the meanings mentioned above and $R^{16}$ represents hydrogen, or a reactive derivative thereof; and the other substituents have the meaning given above; is intramolecularly cyclized, and protecting groups present are removed; or (c) a compound of the formula IV

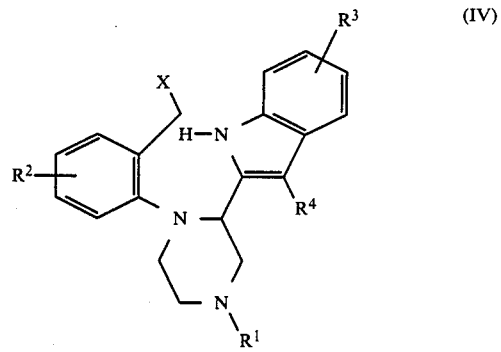

wherein X represents a nucleophilic leaving group and the other substituents have the meanings given above, or a reactive derivative thereof, is intramolecularly cyclized; and, if desired, a compound obtained by one of the processes (a) to (c) is converted into another compound according to the invention, by e.g. esterifying, amidating, decarboxylating or reducing free carboxy $R^4$, or converting esterified or amidated carboxy $R^4$ into free carboxy, or converting a compound of the formula I wherein $R^1$ is hydrogen into a compound of the formula I wherein $R^1$ has the meanings given above except hydrogen, or converting a compound of the formula I wherein $R^1$ has the meanings given above except hydrogen into the 2-N-oxide, or converting the 2-N-oxide into the corresponding compound of the formula I.

The above-mentioned processes and the additional operations are discussed below in more detail. Process (a) is preferred.

Process (a)—A suitable reducing agent is preferably diborane. Alane, alkali-metal aluminum hydrides, e.g. lithium aluminum hydride, sodium tri-tert-butoxyaluminum hydride or sodium bis-(2-methoxy-ethoxy)aluminum hydride are further examples of suitable reducing agents. If $R^{14}$ represents lower alkoxycarbonyl or carbamoyl, some of the above-mentioned reducing agents except borane simultaneously reduce the lower alkoxycarbonyl moiety or carbamoyl moiety.

Preferred are those starting materials of the formula II wherein $R^5$ and $R^6$ together and $R^{10}$ and $R^{11}$ together represent oxo, and $R^8$, $R^9$, $R^{12}$ and $R^{13}$ represent hydrogen, those represented by formula IIA

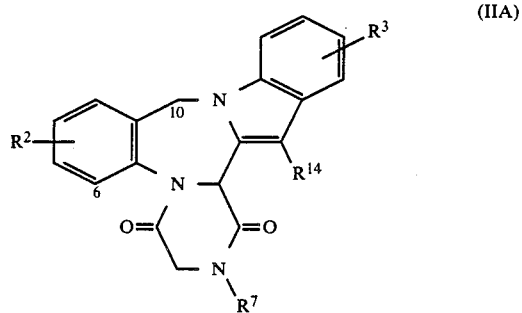
(IIA)

wherein $R^7$ is hydrogen, lower alkyl, $C_{3-7}$-alkenyl bonded on a saturated carbon, $C_{3-7}$-alkynyl bonded on a saturated carbon, 3 to 7 ring-membered cycloalkyl, $C_{2-7}$-alkyl substituted by a substituent selected from hydroxy, amino, N-mono-lower alkyl-amino and N,N-di-lower alkyl-amino wherein said substituents are separated from the ring nitrogen atom by at least 2 carbon atoms; or $R^7$ is lower alkyl substituted by a substituent selected from 3 to 7 ring-membered cycloalkyl, lower alkoxycarbonyl, carbamoyl, and phenyl unsubstituted or substituted by up to three members selected from lower alkyl, lower alkoxy, lower alkylthio, halogen and trifluoromethyl; $R^2$ and $R^3$, independently of one another, represent hydrogen, lower alkyl, hydroxy, lower alkoxy, halogen or trifluoromethyl; and $R^{14}$ represents hydrogen, lower alkyl, hydroxy-lower alkyl, lower alkoxycarbonyl or carbamoyl.

Preferred intermediates are those compounds of formula IIa which can be converted to the preferred embodiments of the invention, particularly the compounds of formula IIA wherein $R^7$ represents hydrogen or lower alkyl; $R^2$ represents hydrogen, lower alkyl, halogen or trifluoromethyl; $R^3$ represents hydrogen, lower alkyl, halogen, trifluoromethyl or lower alkoxy; and $R^{14}$ represents hydrogen, lower alkyl or lower alkoxycarbonyl.

Said starting materials of formula IIA are e.g. prepared by reacting a lower alkyl ester, such as the ethyl ester of the formula V

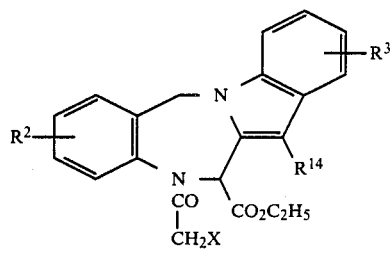
(V)

wherein the substituents $R_2$, $R_3$ and $R_{14}$ have the meanings given above, X represents a leaving group, such as chloro, with an amine of the formula $R^7$—$NH_2$ wherein $R^7$ has the meanings given above with the proviso that amino, lower alkylamino and, if necessary, hydroxy groups present in $R^7$ are protected by suitable amino or hydroxy protecting groups and said protecting groups are later removed.

The starting materials of the formula V are manufactured e.g. by reacting a compound of the formula VI

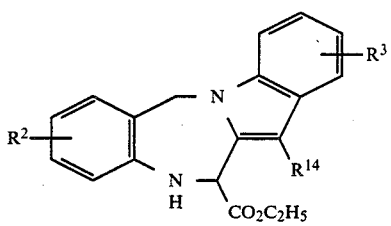
(VI)

wherein the substituents have the meanings given above with the proviso that a hydroxy group present in $R^{14}$ is, if desired, protected by a hydroxy protecting group; with e.g. chloroacetic acid chloride of the formula Cl—$CH_2$—C(=O)—Cl, and later removing said protecting group, is present.

The starting materials of the formula VI are manufactured e.g. by reducing a compound of the formula VII

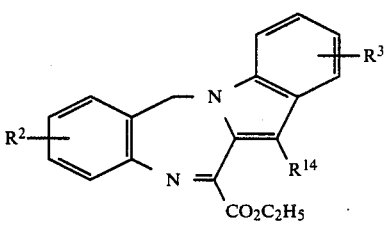
(VII)

wherein the substituents have the meanings given above with e.g. sodium hypophosphite ($NaH_2PO_2$) in the presence of 5% palladium-on-carbon.

The starting materials of the formula VII are manufactured e.g. by intramolecularly cyclizing e.g. a compound of the formula VIII

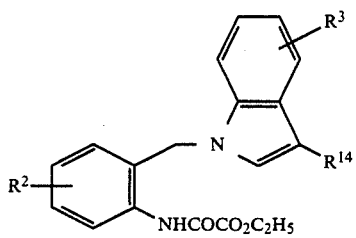

(VIII)

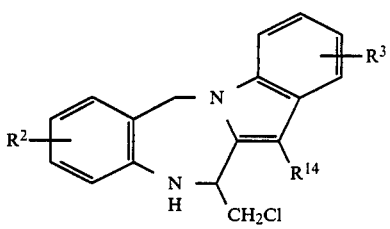

(VIa)

wherein the substituents have the meanings given above by means of e.g. phosphorus oxychloride and phosphorus pentoxide. Preferably, the reaction is carried out using a starting material of the formula VIII wherein $R^{14}$ is lower alkoxycarbonyl. Said lower alkoxycarbonyl substituent $R^{14}$ may be transformed into other substituents, e.g. carboxy, hydroxymethyl, etc. at a later step.

The starting materials of the formula VIII are manufactured e.g. by reacting a compound of the formula IX

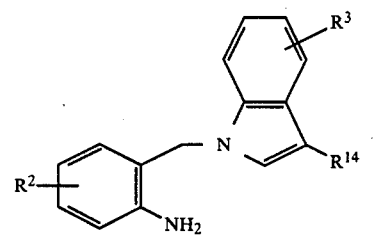

(IX)

with e.g. ethyl oxalyl chloride in the presence of a base such as pyridine.

The starting materials of formula IX are in turn prepared by reduction of the nitro group in the corresponding nitro substituted compound with e.g. iron in acetic acid. The nitro substituted compounds are prepared by treating a compound of the formula X

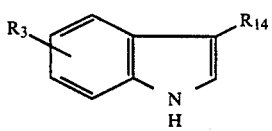

(X)

with e.g. an $R^2$-substituted-o-nitrobenzyl halide in the presence of a strong base, e.g. lithium amide. The starting materials of formula X, e.g. indole-3-carboxylic acid esters, are known in the art.

Alternately, a compound of formula IX is first treated with e.g. chloroacetyl chloride to obtain after cyclization with phosphorous oxychloride/phosphorus pentoxide and reduction of the C=N bond a compound of formula VIa.

Condensation with e.g. chloroacetyl chloride followed by treatment with a compound of formula $R^7NH_2$, appropriately protected if required, yields an intermediate of formula II wherein $R_{10}$ and $R_{11}$ together represent oxo; $R^5$, $R^6$, $R^8$, $R^9$, $R^{12}$ and $R^{13}$ represent hydrogen; $R^2$, $R^3$, $R^7$ and $R^{14}$ have meaning as previously described.

Alternately, a compound of formula VIa is reacted with e.g. ethyl oxalyl chloride followed by treatment with a compound of the formula $R^7NH_2$, appropriately protected as required, to obtain an intermediate of formula II in which $R^8$ and $R^9$ together and $R^{10}$ and $R^{11}$ together represent oxo; $R^5$, $R^6$, $R^{12}$ and $R^{13}$ represent hydrogen; and $R^2$, $R^3$, $R^7$ and $R^{14}$ have meaning as previously defined.

Alternately, a compound of formula VIa is reacted with an appropriately alpha-substituted acetic acid ester, e.g. ethyl bromoacetate, followed by treatment with a compound of the formula $R^7$—$NH_2$, appropriately protected as required, to obtain an intermediate of formula II in which $R^8$ and $R_9$ together represent oxo and $R^5$, $R^6$, $R^{10}$, $R^{11}$, $R^{12}$ and $R^{13}$ represent hydrogen; and $R^2$, $R^3$, $R^7$ and $R^{14}$ have meaning as previously defined above.

Process b—The cyclization according to process (b) can be carried out by heating a solution of a compound of formula III wherein the leaving group X is e.g. chloro in an anhydrous polar solvent, preferably in the presence of an inorganic base such as potassium carbonate, or a tertiary amine such as triethylamine.

The starting materials of formula III e.g. wherein $R^{15}$ represents a leaving group such as chloro and $R^{16}$ represents the group —$CH_2$—$CH_2$—$N(R^7)$—H can be prepared by condensing a compound of formula VIa above with e.g. 1-bromo-2-chloroethane in the presence of a strong base such as sodium hydride in a polar solvent such as dimethylformamide to obtain an intermediate of formula III in which for instance $R^{15}$ represents chloro and $R^{16}$ represents —$CH_2CH_2Cl$, and subsequently reacting said intermediate with an amine of the formula $R^7$—$NH_2$ under conditions of amine alkylation, in an inert solvent, preferably in the presence of a base such as triethylamine or potassium carbonate, and optionally an iodide salt, such as potassium iodide.

Process c—The cyclization according to process (c) can be carried out by treating an intermediate of formula IV with a strong anhydrous base, such as lithium amide.

In the context of the processes cited herein, a leaving group represents preferably a reactive esterified hydroxy group, such being especially halo, for example chloro, bromo or iodo, or aliphatically or aromatically substituted sulfonyloxy, for example methylsulfonyloxy or 4-methylphenylsulfonyloxy (tosyloxy).

The compounds of formula I or intermediates leading thereto can be converted into other compounds of formula I or corresponding intermediates, using chemical methodology known in the art and as illustrated herein.

Compounds of the invention, e.g. those o formula I wherein the nitrogen substituent $R^1$ represents hydrogen may be converted to the compounds wherein $R^1$ represents substituents other than hydrogen, e.g. by (a) reaction with a reactive esterified derivative, e.g. a halide, corresponding to the group $R^1$, or (b) reaction with an aldehyde, e.g. a lower alkylcarboxyldehyde, in the presence of a reducing agent such as sodium cyanoborohydride to yield a compound of formula I wherein $R^1$ represents lower alkyl; or (c) reductive alkylation with formaldehyde and formic acid to yield the compound wherein $R^1$ represents methyl.

Compounds of the invention, e.g. those of formula I wherein $R^1$ is methyl, particularly those wherein $R^4$ represents hydrogen or lower alkyl, can also be prepared by reacting the corresponding compounds wherein $R^1$ represents hydrogen with a lower alkyl- or phenyl-lower alkyl-haloformate, such as ethyl chloroformate, to first obtain compounds wherein $R^1$ is e.g. alkoxycarbonyl or phenylalkoxycarbonyl, and reducing said acyl derivatives with simple or complex light metal hydrides such as lithium aluminum hydride, sodium tri-t-butoxy- or bis-(2-methoxyethoxy)-aluminum hydride.

Compounds wherein the nitrogen substituent represents benzyl or optionally substituted benzyl, may be hydrogenolyzed to the corresponding compounds wherein the nitrogen substituent represents hydrogen, for example with hydrogen in the presence of a hydrogenolysis catalyst, e.g. palladium on charcoal.

Unsaturated N-substituted compounds, such as those bearing an alkenyl or alkynyl radical, may also be hydrogenated with catalytically activated hydrogen to obtain compounds bearing the corresponding N-alkyl radical.

The compounds substituted on aromatic rings by hydroxy (phenols) may be converted to the compounds substituted by lower alkoxy using methods known in the art for the alkylation of phenols, such as reacting a compound of formula I wherein $R^2$ and/or $R^3$ represents hydroxy in the presence of a base, optionally under conditions of phase transfer catalysis with a reactive esterified derivative of the lower alkanol, e.g. a halo derivative thereof.

The conversion of the compounds wherein $R^2$ and/or $R^3$ is lower alkoxy, to the compounds wherein $R^2$ and/or $R^3$ is hydroxy, is carried out by methods well-known in the art, e.g., with a mineral acid, such as hydriodic acid, or, advantageously for compounds wherein lower alkoxy is methoxy, with e.g. boron tribromide in methylene chloride, with sodium or lithium diphenylphosphide in tetrahydrofuran, or by heating with pyridine hydrochloride.

Compounds of the invention and corresponding intermediates, e.g. the compounds of formula I or II wherein e.g. the substituent $R^4$ or $R^{14}$ represents lower alkoxycarbonyl, can be converted to the corresponding carboxylic acids by hydrolysis of the ester, e.g. with aquaous base, such as sodium hydroxide or potassium hydroxide solution.

Compounds of the invention and corresponding intermediates, e.g. the compound of formula I or II wherein $R^4$ or $R^{14}$ represents carboxy can be converted to the corresponding compounds wherein $R^4$ or $R^{14}$ represents hydrogen by using a decarboxylation procedure, e.g. preferably by treatment with a solution of a strong mineral acid, such as hydrochloric acid, at elevated temperature, preferably for several hours.

The said carboxylic acids can also be esterfied to e.g. compounds of formula I or II wherein $R^4$ or $R^{14}$ represents lower alkoxycarbonyl according to known esterification procedures, e.g. by treatment as a reactive functional derivative, such as an acyl halide or a mixed anhydride e.g. derived from a lower alkyl halocarbonate such as ethyl chloroformate, with the appropriate alcohol.

The compounds of the invention and corresponding intermediates, e.g. the compounds of formula I and II wherein $R^4$ or $R^{14}$ represents lower alkoxycarbonyl can be converted to compounds wherein $R^4$ or $R^{14}$ represents carbamoyl, N-mono- or N,N-di-lower alkylcarbamoyl by treatment with anhydrous ammonia or the appropriate N-mono- or N,N-di-lower alkylamine in a polar solvent such as tetrahydrofuran.

The compounds of the invention and corresponding intermediates, e.g. the compounds of formula I or II wherein $R^4$ or $R^{14}$ represents formyl can be prepared from the corresponding compounds of formula I or II wherein $R^4$ or $R^{14}$ represents hydrogen by treatment with dimethylformamide in the presence of phosphorus oxychloride. Compounds wherein $R^4$ represents carboxy can be obtained by oxidation thereof.

The compounds of the invention, e.g. the compounds of formula I wherein $R^4$ represents hydroxymethyl, can be prepared by reduction of the corresponding compounds of formula I wherein $R^4$ represents lower alkoxycarbonyl with a reducing agent such as lithium aluminum hydride or sodium bis-(2-methoxyethoxy)-aluminum hydride. Compounds wherein $R^4$ represents carboxy can be obtained by oxidation thereof.

The compounds of the invention, e.g. the compounds of formula I wherein $R_4$ represents methyl can be prepared by treating a corresponding compounds wherein $R^4$ represents formyl with diborane in tetrahydrofuran.

Tertiary amines of formula I (wherein $R^1$ does not represent hydrogen) can be converted into the corresponding 2-N-oxides, for example with organic peracids, such as lower peralkanoic or perbenzoic acids, e.g. m-chloroperbenzoic acid, advantageously at temperatures at or below room temperature.

In starting compounds and intermediates which are converted to the compounds of the invention in a manner described herein, functional groups present, such as carbonyl (formyl or keto), carboxy, amino and hydroxy and sulfhydryl groups, are optionally protected by conventional protecting groups that are common in organic chemistry. Protected carbonyl, carboxy, amino, hydroxy and sulfhydryl groups are those that can be converted under mild conditions into free carbonyl, carboxy, amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carbonyl group, carboxy group, amino group etc.), the structure and stability of the molecule of which the substituent is a part, and the reaction conditions.

Well-known protecting groups that meet these conditions and their introduciton and removal are described, for example, in J. F. W. McOmie, "Protective Groups in Organic Chemistry", Plenum Press, London, New York 1973, T. W. Greene, "Protective Groups in Organic Synthesis", Wiley, New York 1984, and also in "The Peptides", Vol. I, Schroeder and Luebke, Academic Press, London, New York 1965, as well as in Houben-Weyl, "Methoden der Organischen Chemie", Vol. 15/1, George Thieme Verlag, Stuttgart, 1974.

For instance, a basic primary or secondary amine may be protected in the form of easily cleaved amides, e.g. as acyl derivatives such as the benzyloxycarbonyl (carbobenzyloxy) or the t-butoxycarbonyl derivatives, or any other easily removable N-protecting groups.

A carboxy group may be protected in the form of an easily cleaved ester, e.g. the benzyl ester, the t-butyl ester, and the like as commonly used.

A hydroxy group may be protected in the form of esters, e.g. as acyl derivatives such as the lower alkanoyl, benzyloxycarbonyl or lower alkoxycarbonyl esters, or such hydroxy group may be protected in the form of ethers, e.g. as the 2-tetrahydropyranyl, or benzyl ethers.

In a resulting protected compound of formula I or intermediate, in which one or more of the functional groups are protected, the protected functional groups can be liberated, in a manner, known per se, e.g. by means of solvolysis, e.g. hydrolysis with acid, or by means of reduction, e.g. hydrogenolysis.

The above-mentioned reactions are carried out according to standard methods, in the presence or absence of diluents, preferably such as are inert to the reagents and are solvents thereof, of catalysts, condensing or said other agents respectively, and/or inert atmospheres, at low temperatures, room temperature or elevated temperatures such being preferably near the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions or in which the reaction components are used in the form of their salts or optically pure antipodes. Whenever desirable, the above processes are carried out after first suitably protecting any potentially interfering reactive functional groups, as illustrated above and in the examples herein.

Advantageously, those starting materials should be used in said rections, that lead to the formation of those compounds indicated above as being preferred.

The invention also relates to novel starting materials and processes for their manufacture.

The carbon atom at position 16b of the compounds of the invention represents an asymmetric carbon atom. Said compounds can therefore exist as either racemates or optical isomers (antipodes).

Furthermore, depending on the nature of the substituents involved, the compounds can in addition exist in the form of geometrical isomers or as mixtures of racemates or optical antipodes (diastereoisomeric mixtures).

All the above-cited isomers are to be considered within the scope of the invention.

In case geometric or diastereomeric mixtures of the above compounds or intermediates are obtained, these can be separated into the single isomers by methods in themselves known, e.g. by fractional distillation, crystallization and/or chromatography.

The basic racemic products of formula I or basic intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Any acidic intermediates can be resolved by separation of e.g. the d- and l-(alpha-methylbenzylamine, cinchonidine, cinchonine, quinine, quinidine, ephedrine, dehydroabietylamine, brucine or strychnine)-salts of any compounds having an acidic salt-forming group.

Advantageously, the preferred more active of the antipodes of the compounds of this invention is isolated.

Finally, the compounds of the invention are either obtained in the free form, or as a salt thereof. For example, any resulting free basic amino of formula I can be converted into the corresponding acid addition salts, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or ion exchange preparation.

In view of the close relationship between the free compounds and the compounds in the form of their salts, whenever a compound is referred to in this context, a corresponding salt is also intended, provided such is possible or appropriate under the circumstances.

The compounds of the invention, including their salts, may also be obtained in the form of their hydrates, or include other solvents used for the crystallization.

The present invention additionally relates to the use in mammals of the compounds of formula I and their pharmaceutically acceptable salts, or pharmaceutical compositions thereof, as inhibitors of serotonergic function, particularly as serotonin-2 blockers (antagonists of serotonin at serotonin-2 receptors), for the treatment of disorders responsive to serotonin-2 receptor blockade, namely of psychotropic disorders, such as anxiety, depression or mania, of gastrointestinal disorders such as ulcers, and of cardiovascular disorders such as hypertension.

More specifically, the invention relates to a method of inhiting the effect of serotonin at central serotonin-2 receptors, and advantageously to a method of treatment of psychotropic disorders in mammals, e.g. such responsive to serotonin-2 blockade, particularly anxiety, using an effective amount of a compound of the invention, e.g. of formula I, or of a pharmaceutically acceptable salt thereof as pharmacologically active substances, preferably in the form of pharmaceutically compositions.

The dosage of active compound administered is dependent on the species of warm-blooded animal (mammal), the body weight, age and individual condition, and on the form of administration.

A unit dosage for a mammal of about 50 to 70 kg may contain between about 1 and 50 mg of the active ingredient.

The present invention also relates to the use of the compounds of the invention for the preparation of pharmaceutical compositions, especially pharmaceutical compositions having serotonin receptor modulating activity, particularly serotonin-2 blocking activity.

The pharmaceutical compositions according to the invention are those suitable for enteral, such as oral or rectal, transdermal and parenteral administration to mammals, including man, for the treatment of diseases responsive to the antagonism of serotonin at serotonin-2 receptors, comprising an effective amount of a pharmacologically active compound of formula I or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salts and/or polyethyleneglycol; for tablets also (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (3) adsorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain preferably about 1 to 50% of the active ingredient.

Suitable formulations for transdermal application include an effective amount of a compound of formula I with carrier. Advantageous carriers include absorbable pharmaceutically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is ascertained e.g. by analytical methods, such as microanalysis and spectroscopic characteristics (e.g. MS, IR, NMR).

EXAMPLE 1

A mixture of methyl 1,3,4,16b-tetrahydro-2-methyl-1,4-dioxo-2H,10H-indolo[2,1-c]pyrazino[1,2-a][1,4]benzodiazepine-16-carboxylate (1.48 kg) in tetrahydrofuran (52 L) is heated to reflux under an atmosphere of nitrogen and then a solution of diborane in tetrahydrofuran (1M, 9.47 L) is added over a period of one hour. The reaction mixture is maintained at reflux for 20 hours, at which time it is treated sequentially with methanol (4 L) (slow, cautious addition) and a solution of hydrogen chloride in methanol (7.5N, 1.6 L). The mixture is stirred, refluxed for 2 hours and evaporated in vacuo, and the solid residue obtained is triturated with acetone (4 L) for 1 hour, collected, washed with acetone (4×500 ml) and dried (18 hours, 50°/0.5 mm Hg) to yield methyl 1,3,4,16b-tetrahydro-2-methyl-2H,10H-indolo[2,1-c]pyrazino[1,2-a][1,4]benzodiazepine-16-carboxylate hydrochloride, mp 272°–273°. This salt is suspended in dichloromethane and sufficient ammonium hydroxide (28%) in water is added to liberate the free base. The basic mixture is stirred for 45 minutes, the aqueous layer is removed and discarded and the organic layer is washed with water. The dichloromethane is evaporated in vacuo and the residual foam dissolved in boiling 2-propanol. The solution is filtered to remove a small amount of insolubles, then allowed to cool overnight for complete crystallization. The obtained solid is purified by recrystallization from 2-propanol. The solution is allowed to cool gradually while stirring overnight. The resulting crystals are collected by filtration, washed with 2-propanol and dried (16 hours, 80°/3 mm Hg) to yield methyl 1,3,4,16b-tetrahydro-2-methyl-2H,10H-indolo[2,1-c]pyrazino[1,2-a][1,4]benzodiazepine-16-carboxylate, mp 157°–159°, the compound of formula I wherein $R^1$ is methyl, $R^2$ and $R^3$ are hydrogen and $R^4$ is methoxycarbonyl.

The hydrochloride salt is prepared as follows:

Methanol (20 L) and 2.37 kg of methyl 1,3,4,16b-tetrahydro-2-methyl-2H,10H-indolo[2,1-c]pyrazino[1,2-a][1,4]benzodiazepine-16-carboxylate are combined, heated to reflux, and the mixture is treated with a solution of hydrogen chloride in methanol (7.6N, 870 ml). The reaction mixture is maintained at reflux for 10 minutes and then is allowed to cool gradually to room temperature while stirring overnight. The suspension is filtered and the solid hydrochloride is washed with methanol (2×500 ml) and dried (18 hours, 80°/0.1 mm Hg). The obtained compound is added to boiling water (31 L) and the mixture is stirred at reflux until solution is complete (20 minutes). Heating is then discontinued and the mixture is stirred overnight at 15°, cooled to 5°, filtered and the collected solid is washed with water (1 L). The product is dried (6 hours, 80°/3 mm Hg; 30 hours, 100°/0.1 mm Hg), passed through a 40 mesh screening and dried further (15 hours, 110°/0.1 mm Hg) to give methyl 1,3,4,16b-tetrahydro-2-methyl-2H,10H-indolo[2,1-c]pyrazino[1,2-a][1,4]benzodiazepine-16-carboxylate hydrochloride, mp 275°–277°.

The starting material is prepared as follows:

A solution of trichloroacetyl chloride (5.60 kg) in dichloromethane (3.5 L) is added over a period of 5.5 hours to a cold (5°–10°), stirred mixture of indole (3.50 kg) and pyridine (2.53 kg) in dichloromethane (15 L). The reaction mixture is stirred for 48 hours and filtered to collect crude solid. The filtrate is concentrated to 5 L and a second crop of crude solid is filtered. Both crops are combined and triturated with 1:1 ethanol/water (18 L). After dyring (18 hours, 80°/1 mm Hg) 3-trichloro-acetyl-1H-indole is obtained, mp 231°–234° (dec).

Sodium spheres (0.106 kg) are cautiously added in portions to stirred methanol (20.0 L) under an atmosphere of nitrogen. After the reaction is complete, the solution is cooled to 25° and 3-trichloro-acetyl-1H-indole (5.94 kg) is added in portions over a period of 35 minutes. The mixture is stirred for 2 hours, cooled to 10°, at which time ice-cold water (20 L) is added. Crystalline product is isolated by filtration, washed with 1:1 methanol/water (2 L) and dried (12 hours, 60°/3 mm Hg; 36 hours, 25°/0.1 mm Hg) to yield methyl 1H-indole-3-carboxylate, mp 146°–148°.

Lithium amide (0.416 kg) is added in portions to a stirred solution of methyl 1H-indole-3-carboxylate (3.17 kg) in dimethyl sulfoxide (27 L) at initially 20° under an atmosphere of nitrogen and under external cooling. This is stirred for 1 hour and then 2-nitrobenzyl chloride (3.10 kg) is added in 2 portions within 1 hour. Once addition is complete, the mixture is stirred for 2 hours at room temperature and then poured into vigorously stirred ice cold water (80 L). The precipitate is collected by filtration, triturated with refluxing 2-propanol (12 L) for 1 hour, filtered and air-dried overnight whereupon methyl 1-(2-nitrobenzyl)-1H-indole-3-carboxylate is obtained; mp 129°–132°.

Methyl 1-(2-nitrobenzyl)-1H-indole-3-carboxylate (4.50 kg), glacial acetic acid (27 L) and water (2.7 L) are combined and heated to 65°. Iron filings (3.60 kg) are added in 8 portions over a period of 3 hours. After each addition the mixture is cooled to about 80°. After the addition is complete, the mixture is maintained at 85°–90° for 2 hours, diluted with water (40 L), filtered and the collected solid is washed with water (6×4 L), air-dried overnight, dissolved in dimethylformamide (32 L) and the solution filtered to remove insolubles. The filtrate is added to water (72 L) and the mixture is stirred for 30 minutes, filtered, washed with water (10×3 liters), and dried (120 hours, 60°/0.5 mm Hg) whereupon methyl 1-(2-aminobenzyl)-1H-indole-3-carboxylate is obtained; mp 168°–170°.

Ethyl oxalyl chloride (2.68 kg) is added over a period of 2.5 hours to a stirred mixture of methyl 1-(2-aminobenzyl)-1H-indole-3-carboxylate (5.00 kg), pyridine (1.55 kg) and dichloromethane (50 L) at room temperature under an atmosphere of nitrogen. The reaction mixture is then stirred overnight, washed with 1N hydrochloric acid (10 L) and water (2×15 L), each wash being separated from the lower organic layer and discarded. The slurry of the desired product in dichloromethane is evaporated in vacuo to give a residual solid which is triturated with 2-propanol (6 L), collected and dried (8 hours, 70°/3 mm Hg; 48 hours, 70°/0.1 mm Hg) to yield methyl 1-[2-(ethoxycarbonylcarbonylamino)benzyl]1H-indole-3-carboxylate; mp 174°–177°.

Phosphorus pentoxide (1.00 kg) is added to a stirred suspension of methyl 1-[2-(ethoxycarbonylcarbonylamino)benzyl]-1H-indole-3-carboxylate (1.00 kg) in phosphorus oxychloride (6 L) at room temperature. The reaction mixture is stirred for 30 minutes and then heated to 100° for 1 hour, at which time most of the solvent is removed by distillation at reduced pressure. The oily residue is dissolved in dichloromethane (6 L) and the solution is cautiously poured into a stirred mixture of ice (20 kg) and water (20 L). Additional dichloromethane (16 L) is added and the mixture is stirred for 1 hour. The organic layer is separated and the aqueous layer is extracted with dichloromethane (3×4 L). The combined extracts are evaporated in vacuo to give a solid which is dissolved in toluene at 95°, the mixture being stirred for 3 hours and filtered hot. The filtrate is evaporated in vacuo and the solid residue is triturated with diethyl ether, collected and dried (16 hours, 25°/0.1 mm Hg) to yield 12-ethyl, 13-methyl 6H-indolo[2,1-c][1,4]benzodiazepine-12,13-dicarboxylate, mp 188°–190°.

A solution of sodium hypophosphite monohydrate (3.34 kg) in water (16 liters) is added over a period of 7 hours to a stirred, heated (50°–55°) mixture of 12-ethyl,13-methyl 6H-indolo[2,1-c][1,4]benzodiazepine-12,13-dicarboxylate (3.45 kg), 5% palladium-on-carbon (50% water wet, 286 g) and potassium carbonate (3.34 kg) in tetrahydrofuran (23 L) under an atmosphere of nitrogen. After addition is complete, the reaction mixture is allowed to cool gradually with stirring overnight. The completeness of reaction is evaluated by thin layer chromatography on silica gel plates (85:15 toluene/ethyl acetate) prior to work up. If reduction is incomplete, more carbonate and hypophosphite are added and the reaction mixture is allowed to react for a further period of time. The layers are separated and the aqueous layer is extracted with ethyl acetate (2×8 L). The combined organic layers are filtered and evaporated in vacuo to give a solid which is triturated with diethyl ether (4 L), filtered and dried (6 hours, 60°/3 mm Hg; 18 hours, 60°/0.1 mm Hg) to yield 12-ethyl,13-methyl 11,12-dihydro-6H-indolo[2,1-c][1,4]benzodiazepine-12,13-dicarboxylate; mp 184°–186°.

A mixture of 12-ethyl,13-methyl 11,12-dihydro-6H-indolo[2,1-c][1,4]benzodiazepine-12,13-dicarboxylate (3.40 kg) and chloroacetyl chloride (1.16 kg) in ethyl acetate (28 L) is refluxed for 5 hours and then is allowed to cool while stirring overnight. The reaction mixture is filtered to obtain a solid which is washed with diethyl ether (2×1 L) and dried (18 hours, 80°/3 mm Hg) to yield 12-ethyl,13-methyl 11-(chloroacetyl)-11,12-dihydro-6H-indolo-[2,1-c][1,4]benzodiazepine-12,13-dicarboxylate; mp 231°–233°. A second crop of said compound is obtained by concentration of the filtrate to a small volume.

A stirred mixture of 12-ethyl,13-methyl 11-(chloroacetyl)-11,12-dihydro-6H-indolo-[2,1-c][1,4]benzodiazepine-12,13-dicarboxylate (6.93 kg) in tetrahydrofuran (46 L) is cooled to 5° and then gaseous monomethylamine (5.00 kg) is bubbled in a steady stream beneath the surface of the solvent. The mixture is stirred overnight at room temperature, refluxed for 3 hours, cooled to 20° and filtered. The obtained solid is then washed on the filter with tetrahydrofuran (4×1 L) and triturated with water (20 L) for 1 hour. The suspension is filtered and washed with water (6×4 L). The solid is dried (18 hours, 100°/0.05 mm Hg) to obtain methyl 1,3,4,16b-tetrahydro-2-methyl-1,4-dioxo-2H,10H-indolo[2,1-c]pyrazino[1,2-a][1,4]-benzodiazepine-16-carboxylate, mp 357° (decomposition).

EXAMPLE 2

To a solution of 1 g of methyl 1,3,4,16b-tetrahydro-2-methyl-2H,10H-indolo[2,1-c]pyrazino[1,2-a][1,4]benzodiazepine-16-carboxylate in 25 ml of ethanol is added 15 ml of 5N KOH solution and the reaction is heated at reflux temperature for 3 hours. On cooling the ethanol is removed by evaporation under reduced pressure. The aqueous residue is diluted with 15 ml water and the solution neutralized to pH 6 with acetic acid. The precipitate of 1,3,4,16b-tetrahydro-2-methyl-2H,10H-indolo[2,1-c]pyrazino[1,2-a][1,4]benzodiazepine-16-carboxylic acid is collected; after crystallization from acetone, mp 280°–284°.

EXAMPLE 3

Reduction of 1,3,4,16b-tetrahydro-1,4-dioxo-2-methyl-2H,10H-indolo[2,1-c]pyrazino[1,2-a][1,4]benzodiazepine with diborane in an analagous way to that described in example 1, yields 1,3,4,16b-tetrahydro-2-methyl-2H,10H-indolo[2,1-c]pyrazino[1,2-a][1,4]benzodiazepine hydrochloride, mp 279°–280°.

The starting material is prepared as follows:

A mixture of 9.5 g of methyl 1,3,4,16b-tetrahydro-1,4-dioxo-2-methyl-2H,10H-indolo[2,1-c]pyrazino[1,2-a][1,4]benzodiazepine-16-carboxylate, 95 ml of ethanol and 190 ml of 1N sodium hydroxide is heated at reflux temperature with stirring for 2 hours. The solvent is then removed under reduced pressure to yield the sodium salt of the corresponding carboxylic acid. To this residue is added 95 ml of 6N HCl and 190 ml of tetrahydrofuran and the reaction mixture is heated at reflux temperature for 5 hours. On cooling to room temperature the solvent is evaporated to dryness under reduced pressure and then extracted with a mixture of 200 ml methylene chloride and 100 ml 1N sodium hydroxide. The methylene chloride extract is separated and washed with 50 ml saturated sodium chloride solution. The methylene chloride solution is then dried over anhydrous magnesium sulfate, filtered and the solvent evaporated under reduced pressure to yield 1,3,4,16b-tetrahydro-1,4-dioxo-2-methyl-2H,10H-indolo[2,1-c]pyrazino[1,2-a][1,4]benzodiazepine which is crystallized from ether, mp 188°–189°.

EXAMPLE 4

To the reagent made from 0.56 ml of dimethylformamide in 5 ml methylene chloride and 1.03 g of phosphorous oxychloride is added a solution of 1.88 g of 1,3,4,16b-tetrahydro-2-methyl-2H,10H-indolo[2,1-c]pyrazino[1,2-a][1,4]-benzodiazepine in 5 ml methylene chloride in a dropwise manner maintaining the temperature of the reaction below 10°. The reaction is allowed to stir at room temperature for 30 minutes. The reaction mixture is quenched with 10 ml of a saturated solution of sodium acetate and heated at reflux temperature for 1 hour. On cooling to room temperature the reaction is extracted with 3×50 ml methylene chloride. The organic extracts are combined and dried over anhydrous sodium sulfate and the solvent removed by evaporation under reduced pressure to yield 1,3,4,16b-tetrahydro-2-methyl-2H,10H-indolo[2,1-c]pyrazino[1,2-a][1,4]benzodiazepine-16-carboxaldehyde which is converted to the hydrochloride salt, mp 260°–266°.

EXAMPLE 5

To a solution of 5.4 g of methyl, 1,3,4,16b-tetrahydro-2-methyl-2H,10H-indolo[2,1-c]pyrazino[1,2-a][1,4]benzodiazepine-16-carboxylate in 100 ml tetrahydrofuran is added 1 g of lithium aluminum hydride in small portions over a 10 minute period maintaining the temperature of the reaction below 25°. On completion of the addition the reaction is heated at reflux temperature for 4 hours. On cooling to room temperature the reaction mixture is quenched by the cautious dropwise addition of 0.65 ml of water, then 0.65 ml 15% NaOH solution followed by 1.95 ml water. The reaction mixture is filtered and the filter cake washed thoroughly with 100 ml of methylene chloride. The filtrate is evaporated to dryness under reduced pressure to yield 1,3,4,16b-tetrahydro-2-methyl-16-hydroxymethyl-2H,10H-indolo[2,1-c]pyrazino[1,2-a][1,4]benzodiazepine as an oil which, after crystallization from ether, has mp 184°–189°.

EXAMPLE 6

To a solution of 4.4 g of 1,3,4,16b-tetrahydro-2-ethoxycarbonyl-2H,10H-indolo[2,1-c]pyrazino[1,2-a][1,4]benzodiazepine in 88 ml ethanol is added 24 ml of 50% potassium hydroxide solution. The reaction mixture is heated at reflux temperature for 6 hours. The solvent is evaporated to dryness under reduced pressure and the residue extracted with a mixture of 350 ml of diethyl ether and 250 ml of water. The ethereal extract is washed with water, separated and then dried over anhydrous magnesium sulfate. The solvent is evaporated to yield 1,3,4,16b-tetrahydro-2H,10H-indolo[2,1-c]pyrazino[1,2-a][1,4]benzodiazepine which is converted to the hydrochloride salt, mp 263° dec.

The starting material is prepared as follows:

To a solution of 712 mg of 1,3,4,16b-tetrahydro-2-methyl-2H,10H-indolo[2,1-c]pyrazino[1,2-a][1,4]benzodiazepine in 5 ml toluene is added 1.2 g of ethyl chloroformate and the reaction mixture is heated at reflux temperature with stirring for 8 hours. On cooling to room temperature the reaction mixture is diluted with 50 ml of diethyl ether and the resulting precipitate collected by filtration and washed well with ether. The filtrate is evaporated to dryness under reduced pressure to yield 1,3,4,16b-tetrahydro-2-ethoxycarbonyl-2H,10H-indolo[2,1-c]pyrazino[1,2-a][1,4]benzodiazepine as an oil which is used in the next step without further purification.

EXAMPLE 7

To a solution of 1.4 g of 1,3,4,16b-tetrahydro-2-methyl-2H,10H-indolo[2,1-c]pyrazino[1,2-a][1,4]benzodiazepine-16-carboxaldehyde in 35 ml tetrahydrofuran is added 17 ml of 1M diborane in tetrahydrofuran. The reaction mixture is heated at reflux temperature for 5 hours. The reaction is then treated with 10 ml methanol and 3.5 ml acetic acid and heating is continued for an additional 1 hour. The solvent is evaporated under reduced pressure and the residue is dissolved in methylene chloride and washed with 5% sodium hydroxide solution. The methylene chloride layer is separated and the solvent evaporated under reduced pressure to yield 1,3,4,16b-tetrahydro-2,16-dimethyl-2H,10H-indolo[2,1-c]pyrazino[1,2-a][1,4]benzodiazepine which is converted to the hydrochloride salt, mp 293°–298° dec.

EXAMPLE 8

The following compounds of formula I are prepared using methods analogous to those described in the previous examples:
(a) methyl 1,3,4,16b-tetrahydro-2H,10H-indolo[2,1-c]pyrazino[1,2-a][1,4]benzodiazepine-16-carboxylate hydrochloride, mp 236°–240°;
(b) 1,3,4,16b-tetrahydro-2-n-propyl-2H,10H-indolo[2,1-c]pyrazino[1,2-a][1,4]benzodiazepine hydrochloride, mp 258°–260° dec;
(c) 1,3,4,16b-tetrahydro-16-hydroxymethyl-2-n-propyl-2H,10H-indolo[2,1-c]pyrazino[1,2-a][1,4]benzodiazepine hydrochloride, mp 186°–190°;
(d) 1,3,4,16b-tetrahydro-2H,10H-indolo[2,1-c]-pyrazino[1,2-a][1,4]benzodiazepine-16-carboxamide;
(e) methyl 1,3,4,16b-tetrahydro-2-dimethylaminoethyl-2H,10H-indolo[2,1-c]pyrazino[1,2-a][1,4]benzodidiazepine-16-carboxylate;

(f) methyl 1,3,4,16b-tetrahydro-2-n-propyl-2H,10H-indolo[2,1-c]-pyrazino[1,2-a][1,4]benzodiazepine 16-carboxylate hydrochloride, mp 258°–260°;

(g) 1,3,4,16b-tetrahydro-14-methoxy-2-methyl-2H,10H-indolo[2,1-c]pyrazino[1,2-a][1,4]benzodiazepine hydrochloride, mp 280° dec.;

(h) methyl 1,3,4,16b-tetrahydro-14-methoxy-2-methyl-2H,10H-indolo[2,1-c]pyrazino[1,2-a][1,4]benzodiazepine-16-carboxylate hydrochloride, m.p. 271° dec;

(i) methyl 1,3,4,16b-tetrahydro-7-chloro-2-methyl-2H,10H-indolo[2,1-c]pyrazino[1,2-a][1,4]benzodiazepine-16-carboxylate hydrochloride, m.p. 237° dec.

The following starting materials are prepared e.g. using methods analogous to those described in the previous examples:

(1) methyl 1,3,4,16b-tetrahydro-1,4-dioxo-2H,10H-indolo[2,1-c]pyrazino[1,2-a][1,4]benzodiazepine-16-carboxylate, mp 291° (the material for compound a);

(2) methyl 1,3,4,16b-tetrahydro-1,4-dioxo-2-n-propyl-2H,10H-indolo[2,1-c]pyrazino[1,2-a][1,4]benzodiazepine-16-carboxylate, mp. 298°–300° (the starting material for compounds b and c);

(3) 1,3,4,16b-tetrahydro-1,4-dioxo-2H,10H-indolo[2,1-c]pyrazino[1,2-a][1,4]benzodiazepine-16-carboxamide, mp 292° (the starting material for compound d), which can be obtained by treating starting material 1 above with excess anhydrous ammonia, or as a side product during the preparation of the starting material 1 according to the general process described for the starting material in example 1, but using anhydrous ammonia in the last step;

(4) methyl 1,3,4,16b-tetrahydro-1,4-dioxo-2-dimethylaminoethyl-2H,10H-indolo-[2,1-c]pyrazino[1,2-a][1,4]benzodiazepine-16-carboxylate, mp 222°–224° (the starting material for compound e);

(5) the 1,4-dioxo starting materials for compounds g, h and i from the appropriate 5-substituted indoles according to process described in example 1;

(6) the 1,4-dioxo substituted starting material for compound j starting with 4-chloro-2-nitrobenzyl chloride according to process described in example 1.

EXAMPLE 9

Preparation of 10,000 tablets each containing 10 mg of the active ingredient:
Formula:

| | |
|---|---|
| Methyl 1,3,4,10b-tetrahydro-2-methyl-2H,10H, indolo-[2,1-,C]pyrazino[1,2-a] [1,4]benzodiazepine-16-carboxylate hydrochloride | 100.00 g |
| Lactose | 2,535.00 g |
| Corn starch | 125.00 g |
| Polyethylene glycol 6,000 | 150.00 g |
| Magnesium stearate | 40.00 g |
| Purified water | q.s |

Procedure:

All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

Analogously tablets are prepared, containing about 1–50 mg of one of the other compounds disclosed and exemplified herein.

EXAMPLE 10

Preparation of 1,000 capsules each containing 5 mg of the active ingredient:
Formula:

| | |
|---|---|
| Methyl 1,3,4,10b-tetrahydro-2-methyl-2H,10H, indolo-[2,1-c]pyrazino[1,2-a] [1,4]benzodiazepine-16-carboxylate hydrochloride | 5.0 g |
| Lactose | 212.0 g |
| Modified starch | 80.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filed with 300 mg of said mixture each, using a capsule filling machine.

Analogously capsules are prepared, containing about 1–50 mg of the other compounds disclosed and exemplified herein.

What is claimed is:

1. A compound of the formula

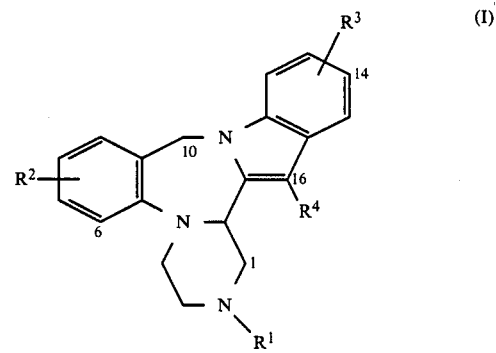

wherein $R^1$ is hydrogen, lower alkyl, $C_{3-7}$-alkenyl bonded on a saturated carbon, $C_{3-7}$-alkynyl bonded on a saturated carbon, 3 to 7 ring-membered cycloalkyl, $C_{2-7}$-alkyl substituted by a substituent selected from hydroxy, amino, N-mono-lower alkyl-amino and N,N-di-lower alkyl-amino wherein said substituents are separated from the ring nitrogen atom by at least 2 carbon atoms; or $R^1$ is lower alkyl substituted by a substituent selected from 3 to 7 ring-membered cycloalkyl, carboxy, lower alkoxycarbonyl, carbamoyl, N-mono-lower alkyl-carbamoyl, N,N-di-lower alkyl-carbamoyl and lower alkanoyl; or $R^1$ is lower alkyl substituted by either phenyl or benzoyl each of said phenyl or benzoyl radicals being unsubstituted or substituted by a member selected from lower alkyl, lower alkoxy, lower alkylthio, halogen and trifluoromethyl; $R^2$ and $R^3$, independently of one another, represent hydrogen, lower alkyl, hydroxy, lower alkoxy, halogen or trifluoromethyl; and $R^4$ represents hydrogen, lower alkyl, hydroxy-lower alkyl, carboxy, lower alkoxycarbonyl, carbamoyl, N-mono- or N,N-di-lower alkyl-carbamoyl, or formyl; or a pharmaceutically acceptable salt thereof; or the 2-N- oxide of any said compound wherein $R^1$ has meaning as defined above but does not represent hydrogen.

2. A compound according to claim 1 of formula I $R^1$ represents hydrogen, lower alkyl, $C_3$-$C_7$ lower alkenyl bonded on a saturated carbon atom or $C_2$-$C_7$-alkyl substituted by hydroxy; $R^2$ and $R^3$ independently represent hydrogen, lower alkyl, lower alkoxy, halogen or trifluoromethyl; $R^4$ represents hydrogen, lower alkyl, hydroxymethyl, carbamoyl, N-mono- or N,N-di-lower alkylcarbamoyl, carboxy or lower alkoxycarbonyl; or a pharmaceutically acceptable salt thereof; or the 2-N-oxide of any said compound wherein $R^1$ is as defined above but does not represent hydrogen.

3. A compound according to claim 2 wherein $R^1$ represents hydrogen or lower alkyl; $R^2$ represents hydrogen, lower alkyl, halogen or trifluoromethyl; $R^3$ represents hydrogen, lower alkyl, halogen, trifluoromethyl or lower alkoxy; $R^4$ represents hydrogen, lower alkyl, hydroxymethyl, carboxy, carbamoyl, N-mono- or N,N-di-lower alkylcarbamoyl or lower alkoxycarbonyl; or a pharmaceutically acceptable salt thereof.

4. A compound according to claim 2 wherein $R^1$ represents hydrogen or lower alkyl; $R^2$ represents hydrogen or halogen; $R^3$ represents hydrogen, lower alkoxy or halogen; $R_4$ represents lower alkoxycarbonyl, carbamoyl or N-mono- or N,N-di-lower alkylcarbamoyl; or a pharmaceutically acceptable salt thereof.

5. A compound according to claim 4 wherein $R^1$ represents hydrogen or lower alkyl; $R^2$ represents hydrogen or halogen; $R^3$ represents hydrogen, lower alkoxy or halogen; $R^4$ represents lower alkoxycarbonyl or carbamoyl; or a pharmaceutically acceptable salt thereof.

6. A compound according to claim 4 wherein $R^1$ represents lower alkyl; $R^2$ and $R^3$ represent hydrogen; $R^4$ represents lower alkoxycarbonyl; or a pharmaceutically acceptable salt thereof.

7. A compound according to claim 3 being 1,3,4,16b-tetrahydro-2-methyl-2H,10H-indolo[2,1-c]pyrazino-[1,2-a][1,4]benzodiazepine or a pharmaceutically acceptable salt thereof.

8. A compound according to claim 3 being methyl 1,3,4,16b-tetrahydro-2-methyl-2H,10H-indolo[2,1-c]pyrazino[1,2-a][1,4]benzodiazepine-16-carboxylate or a pharmaceutically acceptable salt thereof.

9. A pharmaceutically composition suitable for inhibiting the effect of serotonin at serotonin-2 receptors in a mammal comprising an effective serotonin-2 receptor blocking amount of a compound of claim 1 in combination with one or more pharmaceutically acceptable carriers.

10. A method of inhibiting the effect of serotonin at serotonin-2 receptors in a mammal comprising the administration to a mammal in need thereof of an effective serotonin-2 receptor blocking amount of a compound of claim 1 or of a pharmacetutical composition comprising a compound of claim 1 in combination with one or more pharmaceutically acceptable carriers.

11. A method of treating central nervous system, cardiovascular or gastrointestinal disorders responsive to serotonin-2 receptor blockade in a mammal comprising the administration to a mammal in need thereof of an effective serotonin-2 receptor blocking amount of a compound of claim 1 or of a pharmaceutical composition comprising a compound of claim 1 in combination with one or more pharmaceutically acceptable carriers.

12. A method according to claim 11 of treating anxiety.

13. A method of treating anxiety in a mammal comprising the administration to a mammal in need thereof of an effective serotonin-2 receptor blocking amount of a compound of claim 8 or a pharmaceutical composition comprising a compound of claim 8 in combination with one or more pharmaceutically acceptable carriers.

14. A compound of the formula

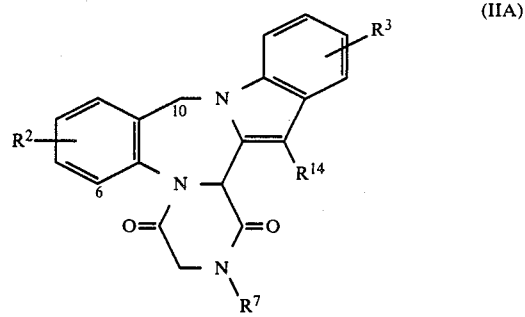

(IIA)

wherein $R^7$ is hydrogen, lower alkyl, $C_{3-7}$-alkenyl bonded on a saturated carbon, $C_{3-7}$-alkynyl bonded on a saturated carbon, 3 to 7 ring-membered cycloalkyl, $C_{2-7}$-alkyl substituted by a substituent selected from hydroxy, amino, N-mono-lower alkyl-amino and N,N-di-lower alkyl-amino wherein said substituents are separated from the ring nitrogen atom by at least 2 carbon atoms; or $R^7$ is lower alkyl substituted by a substituent selected from 3 to 7 ring-membered cycloalkyl, lower alkoxycarbonyl, carbamoyl, and phenyl unsubstitutd or substituted by a member selected from lower alkyl, lower alkoxy, lower alkylthio, halogen and trifluoromethyl; $R^2$ and $R^3$ independently of one another, represent hydrogen, lower alkyl, hydroxy, lower alkoxy, halogen or trifluoromethyl; and $R^{14}$ represents hydrogen, lower alkyl, hydroxy-lower alkyl, lower alkoxycarbonyl or carbamoyl.

15. A compound of claim 13 wherein $R^7$ represents hydrogen or lower alkyl; $R^2$ represents hydrogen, lower alkyl, halogen or trifluoromethyl; $R^3$ represents hydrogen, lower alkyl, halogen, trifluoromethyl or lower alkoxy; and $R^{14}$ represents hydrogen, lower alkyl or lower alkoxycarbonyl.

* * * * *